US00PP14989P2

(12) United States Plant Patent
de Jong

(10) Patent No.: US PP14,989 P2
(45) Date of Patent: Jul. 6, 2004

(54) AGAPANTHUS PLANT NAMED 'BLUE HEAVEN'

(50) Latin Name: *Agapanthus africanus*
Varietal Denomination: Blue Heaven

(76) Inventor: Kees C. J. de Jong, Noordeinde 165 B, Rejerskoop 313, Boskoop (NL), 2771 BL ( * ) Notice: Subject to any disclaimer, the term of this patent is extended or adjusted under 35 U.S.C. 154(b) by 0 days.

(21) Appl. No.: 10/668,015

(22) Filed: Sep. 23, 2003

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2003/01, GTI Jouve Retrieval Software, Citation for 'Blue Heaven'.*

* cited by examiner

*Primary Examiner*—Anne Marie Grunberg
*Assistant Examiner*—Annette H Para

(57) ABSTRACT

A new cultivar of Agapanthus named 'Blue Heaven' that is characterized by an upright, clumping habit, green leaves, perpetual blooming and profuse production of violet-blue flowers. In combination these traits set 'Blue Heaven' apart from all other existing varieties of Agapanthus known to the inventor.

2 Drawing Sheets

Genus: Agapanthus
Species: *africanus*
Denomination: Blue Heaven

BACKGROUND OF THE INVENTION

The present invention relates to a new and distinct cultivar of lily-of-the-Nile grown for use as an ornamental for container, landscape and cut flowers. The new cultivar is known botanically as *Agapanthus africanus* and will hereinafter be referred to as 'Blue Heaven'.

'Blue Heaven' is a chance seedling that was discovered by the inventor in Roelofarendsveen, The Netherlands in 1998. 'Blue Heaven' was discovered as an individual chance seedling in an established block of unknown cultivars of *Agapanthus africanus* being grown for the purpose of cut flower production. 'Blue Heaven' was selected, by the inventor, for the unique traits of abundant quantity of flowers and perpetual blooming.

The new variety 'Blue Heaven' is a chance hybrid that resulted from the open pollination of unknown cultivars of Agapanthus grown from bulbs in a cultivated area of The Netherlands. The female parent, is presumed to be an unknown cultivar of *Agapanthus africanus* and the male parent is presumed to be an unknown cultivar of *Agapanthus africanus.* The unique traits that distinguish 'Blue Heaven' from the parent plants are quantity of flowers and perpetual flowering through the entire season.

'Blue Heaven' is an herbaceous perennial, exhibiting an upright clumping growth habit, dark violet-blue flowers and green foliage. The unique traits of profuse quantity of flowers and perpetual blooming distinguish 'Blue Heaven' from all other existing Agapanthus known to the inventor. There are no comparison plants known to the inventor.

'Blue Heaven' was first asexually propagated in 1999 in a cultivated area of Roeloforendsveen, The Netherlands by the inventor. The method used for asexual propagation was division. Since that time under careful observation, successive generations have been determined stable and true to type. Asexual propagation can also be accomplished using the method of tissue culture.

The Inventor filed on May 28, 1999 application No. 1999/0782 for a grant of European Community Plant Breeder's Rights. Application was granted on Jun. 3, 2002 (Grant No. 9477). The Inventor has been engaged in the build-up of stock, by division, solely at Inventor's own nursery. No plants of 'Blue Heaven' have been sold or otherwise distributed from the Inventor's nursery prior to May 13, 2003.

SUMMARY OF THE INVENTION

The following traits have been repeatedly observed and represent the distinguishing characteristics of the new Agapanthus variety known as 'Blue Heaven'. These traits in combination distinguish 'Blue Heaven' from all other existing varieties of Agapanthus known to the inventor. 'Blue Heaven' has not been tested under all possible conditions and phenotypic differences may be observed with variations in environmental, climatic, and cultural conditions, however, without any variance in genotype.

1. Agapanthus 'Blue Heaven' Evergreen.
2. Agapanthus 'Blue Heaven' flowers perpetually through the entire season.
3. Agapanthus 'Blue Heaven' exhibits 70–80 dark violet-blue flowers per inflorescence.
4. Agapanthus 'Blue Heaven' exhibits an upright and clumping habit. Agapantus 'Blue Heaven' is an ornamental herbaceous perennial.
5. Agapanthus 'Blue Heaven' exhibits green foliage.
6. Agapanthus 'Blue Heaven' is suitable for cut flowers, and as a container or landscape plant.
7. Agapanthus 'Blue Heaven' is 90 cm. in height and 75 cm. in width at maturity.
8. Agapanthus 'Blue Heaven' is hardy to USDA Zone 8b.

BRIEF DESCRIPTION OF THE DRAWINGS

The accompanying color drawings illustrates the overall appearance of the new Agapanthus variety 'Blue Heaven' at three years old and grown in a container, showing the colors as true as it is reasonably possible to obtain in colored reproductions of this type.

The drawing on sheet 1 illustrates the entire plant in bloom from a side perspective.

The drawing on sheet 2 shows a close-up view of the flowers. Colors in the drawings may differ from the color values cited in the detailed botanical description, which accurately describe the actual colors of the new variety 'Blue Heaven'.

The drawings were made using conventional photographic techniques and although flower and foliage colors may appear different from actual colors due to light reflectance, they are as accurate as possible by conventional photography.

BOTANICAL DESCRIPTION OF THE PLANT

The following is a detailed description of the new Agapanthus cultivar named 'Blue Heaven'. Color determinations are in accordance with The 2001 Horticultural Society Colour Chart except where general color terms of ordinary dictionary significance are used. The growing requirements are similar to the species.

Botanical classification: Agapanthus 'Blue Heaven'.
Commercial classification: Ornamental.
Species: *africanus*.
Common name: Lily-of-the-Nile.
Use: Ornamental plant suitable for massing in landscape, container plant or cut flowers.
Type: Herbaceous perennial.
Parentage: The chance hybrid 'Blue Heaven' is presumed to have resulted from the open pollination of unknown cultivars of the following Agapanthus plants:
- *Presumed female parent plant.*—Unknown cultivar of *Agapanthus africanus* Grown from bulb.
- *Presumed male parent plant.*—Unknown cultivar of *Agapanthus africanus* grown from bulb.

Growth rate: Slow growing, an average of 2 shoots per year.
Growth habit: Upright, clumping habit.
Plant height (at maturity): 90 cm. in height.
Plant width (at maturity): 75 cm. in width.
Plant shape: Fountain-shaped, with arching leaves and vertical flower stalks.
Hardiness: USDA Zone 8b.
Propagation: Asexual propagation is accomplished using division or tissue culture.
Root system: Fleshy.
Pollination requirements: None observed.
Sexuality: Monoecious flowers
Cultural requirements: Plant in full sun and well-drained sandy soil.
Cropping time: Approximately 12 months from division to a 1-liter container.
Seasonal interest: Spring, summer and fall flowers.
Diseases and pests: Protect from snails and slugs. No serious problems known to the inventor.
Special growing considerations: Avoid allowing plant to become dry.
Foliage:
- *Type.*—Evergreen.
- *Leaf shape.*—Narrow linear.
- *Leaf form.*—Arching.
- *Branching habit.*—Basal.
- *Leaf apex.*—Acute.
- *Leaf base.*—Broad cuneate.
- *Leaf division.*—Simple.
- *Leaf attachment.*—Sessile.
- *Leaf margins.*—Entire.
- *Leaf color (adaxial surface).*—Closest to 146A.
- *Leaf color (abaxial surface).*—Closest to 136A.
- *Leaf surface (adaxial surface).*—Glabrous and slightly concave.
- *Leaf surface (abaxial surface).*—Glabrous.
- *Pubescence.*—None.
- *Venation pattern.*—Parallel.
- *Color of veins (abaxial and adaxial surfaces).*—146D.
- *Leaf length.*—65 cm. in length.
- *Leaf width.*—3 cm. in width.
- *Leaf fragrance.*—None observed.
- *Stipules.*—None observed.

Flower:
- *Flowering months.*—From early May until the first frost.
- *Inflorescence type.*—Umbel.
- *Number of flowers per umbel.*—75–80 flowers per umbel.
- *Persistent or self-cleaning.*—Self-cleaning.
- *Flower type.*—Solitary.
- *Pedicel color.*—Green, 143A, tending to more yellow green, 147A, at base of flower.
- *Pedicel dimensions.*—Length (average) 5.4 cm length; 1.5 mm in width.
- *Pedicel shape.*—Circular.
- *Pedicel surface.*—Smooth, slightly glossy.
- *Flower bud description at approximately five days prior to opening.*—Shape: Narrow, obovate. Dimensions: Length (average) 2.3 cm in length; 8 mm average width. Color: Violet blue 94A and 94B (both present). Surface: Smooth, slightly glossy.
- *Flower aspect.*—Facing upward and outward.
- *Flower dimensions.*—4.3 cm. in length and 5 cm. in width.
- *Depth of corolla tube.*—1.1 cm. in depth.
- *Dimensions of scape.*—Average of 90 cm. in length and 13–18 mm. in width.
- *Scape color.*—146D.
- *Scape texture.*—Pithy.
- *Shape of scape.*—Cylindrical and slightly tortuous.
- *Scape surface.*—Glabrous.
- *Flower shape.*—Campanulate.
- *Petals.*—Apetalous.
- *Number of tepals.*—Six in number.
- *Tetals fused or unfused.*—Basally fused.
- *Tepal shape.*—Narrow obovate.
- *Tepal margin.*—Entire.
- *Tepal surface (adaxial surface).*—Glabrous.
- *Tepal surface (abaxial surface).*—Glabrous.
- *Tepal color.*—Both 96B and 96D are individually present on an individual tepal.
- *Tepal dimensions.*—3.50 cm. in length and 1 cm. in width.
- *Flower fragrance.*—None.

Reproductive organs:
- *Stamens.*—6 in number.
- *Stamen color.*—94D.
- *Stamen dimensions.*—3 cm. in length; 1 mm in width.
- *Stigma color.*—155A.
- *Anther dimensions.*—Dorsifixed, kidney-shaped, average length: 2 mm.
- *Anther color.*—Brown, 200A.

*Pistil dimensions.*—One present, 2.7 cm in length, of which length of pistil style 2.65 cm.

*Pistil color.*—Violet-blue, 92B at top; white at base.

*Filament dimensions.*—Length (average) 3.5 cm.

*Filament color.*—Violet-blue 92B at top, to white 155C at base.

*Pollen quantity.*—Much, color: yellow-green, 146D.

*Ovary shape.*—Obovate to elliptic.

*Ovary position.*—Inferior.

*Ovary dimensions.*—Length (average) 1.1 cm; width (average) 5 mm.

*Ovary color.*—Yellow-green, between 145C and 150D.

Seed production:

*Number of seeds.*—Average of four per capsule.

*Seed shape.*—Flat and oval.

*Fruit.*—Capsule.

*Fruit color.*—Off-white.

*Fruit size.*—Moderately large.

*Fruit shape.*—Flattened and oblong.

*Fruit surface.*—Glossy.

*Seed size.*—Moderately large.

*Seed color.*—Dark brown to black.

*Seed surface.*—Waxy.

What is claimed is:

1. A new and distinct variety of Agapanthus plant named 'Blue Heaven' as described and illustrated.

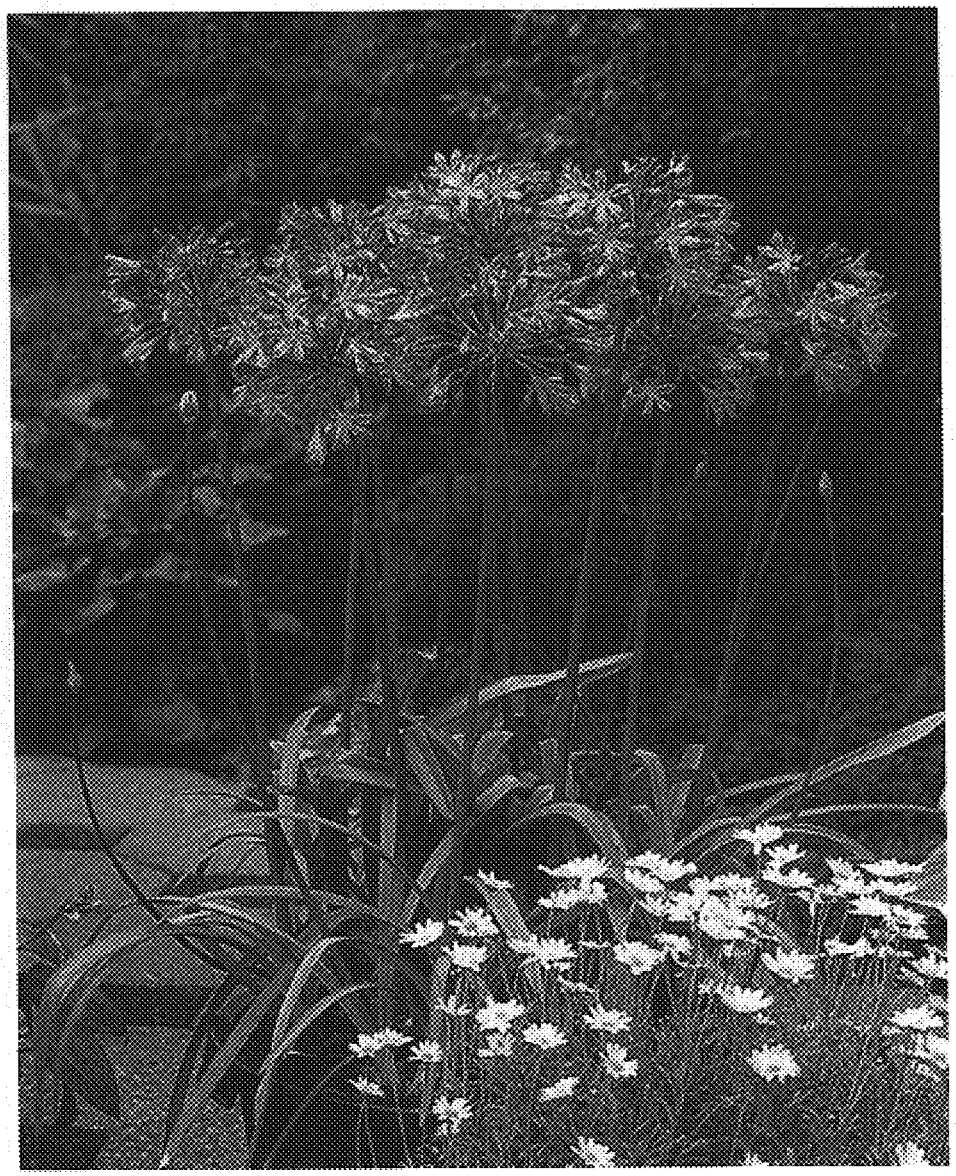

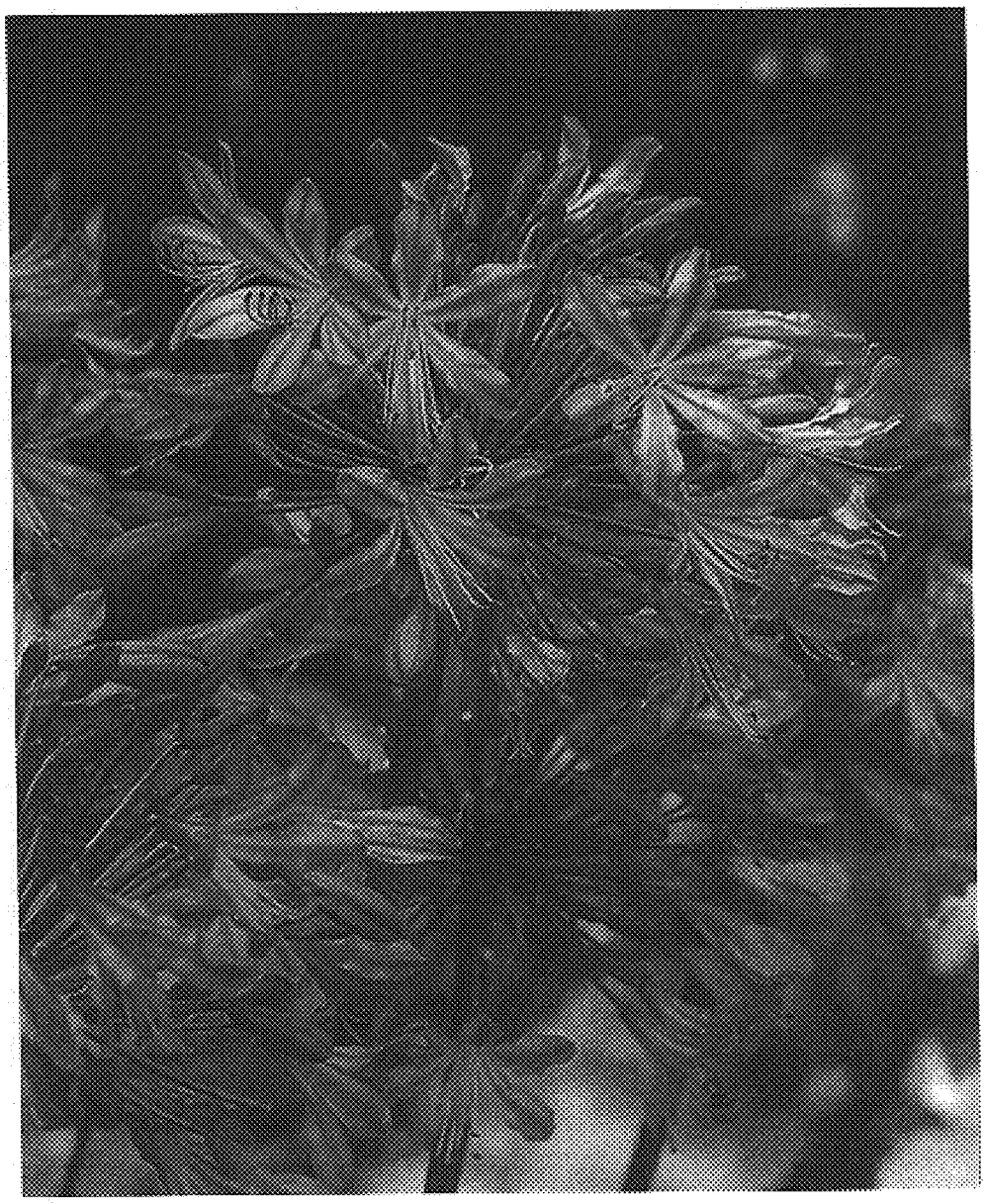

* * * * *